(12) United States Patent
Min

(10) Patent No.: US 8,972,009 B2
(45) Date of Patent: Mar. 3, 2015

(54) SYSTEMS AND METHODS FOR DETERMINING OPTIMAL INTERVENTRICULAR PACING DELAYS BASED ON ELECTROMECHANICAL DELAYS

(75) Inventor: Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 947 days.

(21) Appl. No.: 12/976,419

(22) Filed: Dec. 22, 2010

(65) Prior Publication Data

US 2012/0165890 A1    Jun. 28, 2012

(51) Int. Cl.
  *A61N 1/365*  (2006.01)
  *A61N 1/362*  (2006.01)
  *A61N 1/368*  (2006.01)

(52) U.S. Cl.
  CPC ............ *A61N 1/3627* (2013.01); *A61N 1/3684* (2013.01); *A61N 1/36521* (2013.01); *A61N 1/36564* (2013.01); *A61N 1/36578* (2013.01)
  USPC .......................................................... 607/25

(58) Field of Classification Search
  USPC .................................................... 607/23, 25
  See application file for complete search history.

(56) References Cited

U.S. PATENT DOCUMENTS

| | | | |
|---|---|---|---|
| 6,477,406 | B1 | 11/2002 | Turcott |
| 7,092,759 | B2 * | 8/2006 | Nehls et al. ............ 607/19 |
| 7,139,609 | B1 | 11/2006 | Min et al. |
| 7,248,925 | B2 | 7/2007 | Bruhns et al. |
| 2003/0055345 | A1 | 3/2003 | Eigler et al. |
| 2006/0178589 | A1 | 8/2006 | Dobak, III |
| 2008/0021336 | A1 | 1/2008 | Dobak, III |
| 2009/0306732 | A1 | 12/2009 | Rosenberg et al. |
| 2009/0306736 | A1 | 12/2009 | Dobak, III |

FOREIGN PATENT DOCUMENTS

WO    2006086435    8/2006

* cited by examiner

*Primary Examiner* — Mark W Bockelman

(57) ABSTRACT

Techniques are provided for use with implantable medical devices such as pacemakers for optimizing interventricular (VV) pacing delays for use with cardiac resynchronization therapy (CRT). In one example, ventricular electrical depolarization events are detected within a patient in which the device is implanted. The onset of isovolumic ventricular mechanical contraction is also detected based on cardiomechanical signals detected by the device, such as cardiogenic impedance (Z) signals, S1 heart sounds or left atrial pressure (LAP) signals. Then, an electromechanical time delay (T_Q-toVC) between ventricular electrical depolarization and the onset of isovolumic ventricular mechanical contraction is determined. VV pacing delays are set to minimize the time delay to the onset of isovolumic ventricular mechanical contraction. Various techniques for identifying the onset of isovolumic ventricular contraction based on Z, S1 or LAP or other cardiomechanical signals are described. In some examples, CRT nonresponders are specifically identified and/or heart failure progression is tracked.

13 Claims, 13 Drawing Sheets

US 8,972,009 B2

SYSTEMS AND METHODS FOR DETERMINING OPTIMAL INTERVENTRICULAR PACING DELAYS BASED ON ELECTROMECHANICAL DELAYS

FIELD OF THE INVENTION

The invention generally relates to implantable cardiac rhythm management devices such as pacemakers and implantable cardioverter-defibrillators (ICDs) and cardiac resynchronization therapy (CRT) devices and, in particular, to techniques for determining preferred or optimal interventricular (VV) pacing delays for use in pacing the ventricles using such devices and for identifying and addressing CRT nonresponders.

BACKGROUND OF THE INVENTION

Clinical studies related to cardiac pacing have shown that an optimal atrioventricular pacing delay (e.g., AV delay or PV delay) and/or an optimal interventricular pacing delay (e.g., VV delay) can improve cardiac performance. However, such optimal delays depend on a variety of factors that may vary over time. Thus, what is "optimal" may vary over time. An optimization of AV/PV pacing delay and/or VV pacing delay may be performed at implantation and sometimes, a re-optimization may be performed during a follow-up consultation. While such optimizations are beneficial, the benefits may not last due to changes in various factors related to device and/or cardiac function.

The following patents and patent applications set forth various systems and methods for allowing a pacemaker, ICD, CRT or other cardiac rhythm management (CRM) device to determine and/or adjust AV/PV/VV pacing delays so as to help maintain the pacing delays at optimal values: U.S. patent application Ser. No. 10/703,070, filed Nov. 5, 2003, entitled "Methods for Ventricular Pacing"; U.S. patent application Ser. No. 10/974,123, filed Oct. 26, 2004; U.S. patent application Ser. No. 10/986,273, filed Nov. 10, 2004; U.S. patent application Ser. No. 10/980,140, filed Nov. 1, 2004; U.S. patent application Ser. No. 11/129,540, filed May 13, 2005; U.S. patent application Ser. No. 11/952,743, filed Dec. 7, 2007. See, also, U.S. patent application Ser. No. 12/328,605, filed Dec. 4, 2008, entitled "Systems and Methods for Controlling Ventricular Pacing in Patients with Long Intra-Atrial Conduction Delays"; U.S. patent application Ser. No. 12/132,563, filed Jun. 3, 2008, entitled "Systems and Methods for determining Intra-Atrial Conduction Delays using Multi-Pole Left Ventricular Pacing/Sensing Leads"; and U.S. patent application Ser. No. 12/639,881, filed Dec. 16, 2009, entitled "Systems and Methods for Determining Ventricular Pacing Sites for use with Multi-Pole Leads." See, further, U.S. Pat. No. 7,248,925, to Bruhns et al., entitled "System and Method for Determining Optimal Atrioventricular Delay based on Intrinsic Conduction Delays." At least some of the techniques are implemented within the QuickOpt™ systems of St. Jude Medical.

In particular, intracardiac electrogram (IEGM)-based techniques are set forth within at least some of these documents for exploiting various inter-atrial and interventricular conduction delays observed within the IEGM to determine preferred or optimal VV pacing delays for use in delivering CRT. Briefly, CRT seeks to normalize asynchronous cardiac electrical activation and resultant asynchronous contractions associated with congestive heart failure (CHF) by delivering synchronized pacing stimulus to both ventricles. The stimulus is synchronized so as to improve overall cardiac function. This may have the additional beneficial effect of reducing the susceptibility to life-threatening tachyarrhythmias.

IEGM-based methods for the optimization of VV delays are generally based on the hypothesis that minimizing electrical activation time in the left ventricle (LV) can lead to improved mechanical synchrony in many CRT patients. That is, pacing is directed toward reducing the width of ventricular depolarization events (QRS complexes.) However, in some patients, achieving a shorter paced QRS width (with biventricular pacing) does not result in significant improvement in mechanical synchrony due to functional blocks formed during biventricular pacing. This phenomenon appears to be specific to so-called CRT nonresponders. New methods for improving mechanical synchrony in this group of patients would be helpful in reducing the number of CRT nonresponders.

Accordingly, it would be desirable to provide improvements in the determination of preferred or optimal VV pacing delays for use with CRT and aspects of the present invention are directed to that general goal. In particular, it would be desirable to provide techniques for identifying optimal ventricular pacing locations/vectors and for setting optimal VV pacing delays so as to allow CRT to be delivered more effectively within patients otherwise considered to be CRT nonresponders.

SUMMARY OF THE INVENTION

In a first exemplary embodiment, a method is provided for controlling the delivery of cardiac pacing therapy by an implantable cardiac rhythm management device for implant within a patient. Briefly, ventricular electrical depolarization events are detected within the patient based on electrocardiac signals sensed by the device. The onset of isovolumic ventricular mechanical contraction is also detected within the patient based on cardiomechanical signals detected by the device. Then, an electromechanical time delay between ventricular electrical depolarization and the onset of isovolumic ventricular mechanical contraction is determined. VV pacing delays are set so as to minimize the time delay to the onset of isovolumic ventricular mechanical contraction. Thereafter, pacing is then controlled based on the VV pacing delays. By setting VV pacing delays based on electromechanical time delays that account for the timing of ventricular mechanical contractions, VV delays can be more effectively timed within at least some patients, particularly patients who might otherwise be regarded as CRT nonresponders. Additionally or alternatively, the electromechanical time delay may be used to monitor, track or trend heart failure within the patient.

In an illustrative example, the implantable device is a pacemaker, ICD or CRT device. A left ventricular (LV) intracardiac electrogram (IEGM) is analyzed to detect the peak of the depolarization waveform (QRS complex). The electromechanical time delay is measured between the peak of the LV QRS complex and the onset of isovolumic ventricular contraction ('VC') as detected using, for example, cardiogenic impedance, left atrial pressure (LAP), right ventricular pressure (RVP), left ventricular pressure (LVP), photo-plethysmography (PPG) signals, S1 heart sounds or other suitable cardiomechanical signal parameters measured within the patient. This electromechanical delay is referred to herein as 'T_QtoVC'.

In an embodiment wherein impedance is exploited, values representative of electrical cardiogenic impedance (Z) are detected along a vector extending through the ventricles of the heart of the patient. The rate of change in the cardiogenic impedance (i.e. dZ/dt) is detected and the onset of isovolumic ventricular mechanical contraction can be detected from the dZ/dt values. In one specific example, a bipolar electrical current injection vector is employed between RV tip and LV tip electrodes. A bipolar impedance-responsive voltage sensing vector is employed between LV ring and RV ring electrodes. In another specific example, the bipolar electrical current injection vector is instead between RV tip and ring electrodes. The bipolar impedance-responsive voltage sensing vector is instead between LV tip and ring electrodes. Hybrid vectors can be used as well.

In an embodiment wherein heart sounds are exploited, the peak of an absolute value of an envelope of the S1 heart sound is detected using an implantable acoustic sensor or sensing technique. The onset of isovolumic ventricular mechanical contraction is deemed to correspond to the timing of peak of S1. In an embodiment wherein LAP is exploited, first and second peaks in LAP are detected (subsequent to the QRS complex of the LV IEGM) using an implantable pressure sensor or sensing technique. The onset of isovolumic contraction is deemed to correspond to the timing of a valley or trough between the first and second peaks. Insofar as LVP, RVP and PPG are concerned, the time rate of change in the signal can be detected and the onset of isovolumic contraction derived therefrom. In some cases, the onset of isovolumic contraction can coincide with the peak in the rate of change (i.e. $d^2VLP/dt^2$, $dRVP^2/dt^2$ or $dPPG^2/dt^2$.), depending upon the particular vector.

In a 'stand alone' embodiment, to determine the preferred or optimal value for VV, optimal AV/PV delays are initially determined using existing IEGM-based optimization techniques, such as one of the aforementioned QuickOpt techniques. Then, while pacing is delivered using the optimal AV/PV delays, the VV pacing delay is varied throughout a range of permissible values. T_QtoVC is concurrently tracked using one or more cardiomechanical parameters (e.g., cardiogenic impedance, LAP, S1 heart sounds, etc.) The particular value for VV that yields the shortest T_QtoVC electromechanical delay is then selected as the preferred or optimal VV value.

In a 'combined' embodiment, optimal AV/PV delays—as well as VV delays—are initially determined using existing IEGM-based optimization techniques, such as one of the aforementioned QuickOpt techniques. Pacing is delivered using these initial values. T_QtoVC is measured and compared against a threshold indicative of an acceptable electromechanical delay. So long as the measured value for T_QtoVC does not exceed the threshold, the VV delay is deemed to be sufficient and pacing is delivered using the initial optimized values for AV/PV/VV. However, if T_QtoVC is greater than the threshold (indicating an unacceptably long electromechanical delay), the device then varies the VV pacing delay throughout its range of permissible values. T_QtoVC is tracked and the particular value for VV that yields the shortest T_QtoVC electromechanical delay is identified. This shortest value for T_QtoVC is compared against the threshold and, if it exceeds the threshold (i.e. electromechanical delay is still too long), the patient is deemed to be a CRT nonresponder (or further steps are taken to improve electromechanical synchrony such as by repositioning the leads of the device or by selecting a different VV pacing vector from among the available electrodes of the lead system.) Assuming, though, that the shortest T_QtoVC value is found to be no greater than the threshold, the corresponding VV pacing delay is then selected for use in delivering CRT (along with the previously determined AV/PV delays.) Thus, the 'combined' technique can exploit both IEGM-based VV optimization as well as additional T_QtoVC-based optimization.

In a second exemplary embodiment, a method is provided for identifying preferred or optimal pacing locations for use in delivering of cardiac pacing therapy by an implantable cardiac rhythm management device. Ventricular electrical depolarization events are detected within the patient, and the onset of isovolumic ventricular mechanical contraction is also detected. The electromechanical time delay between ventricular electrical depolarization and the onset of isovolumic ventricular mechanical contraction is then determined. Pacing locations are selected so as to minimize the time delay to the onset of isovolumic ventricular mechanical contraction. Thereafter, pacing is delivered using the selected locations, while preferably using VV pacing delay optimized using the aforementioned T_QtoVC-based techniques. Depending upon the particular embodiment, pacing locations may be selected by choosing among a set of different pacing vectors available with the lead system or by repositioning the leads, or both. For multi-pole leads, a wide variety of vectors may be selectable such that repositioning of the lead might not be needed.

In a third exemplary embodiment, a method is provided for identifying CRT nonresponders for use with implantable cardiac rhythm management device. Ventricular electrical depolarization events and the onset of isovolumic ventricular mechanical contraction are both detected. The electromechanical time delay between ventricular electrical depolarization and the onset of isovolumic ventricular mechanical contraction is determined. The VV pacing delay sufficient to minimize the time delay is determined, such as by using the aforementioned techniques wherein VV delays are varied through a range of values while tracking T_QtoVC. A determination of whether the patient is a CRT nonresponder is then made based on the minimized time delay, such as by comparing the time delay achieved at optimal AV/PV and VV delays to the aforementioned threshold indicative of an acceptable electromechanical delay.

System and method implementations of the various exemplary embodiments are presented herein.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Medical System

Figure 1:
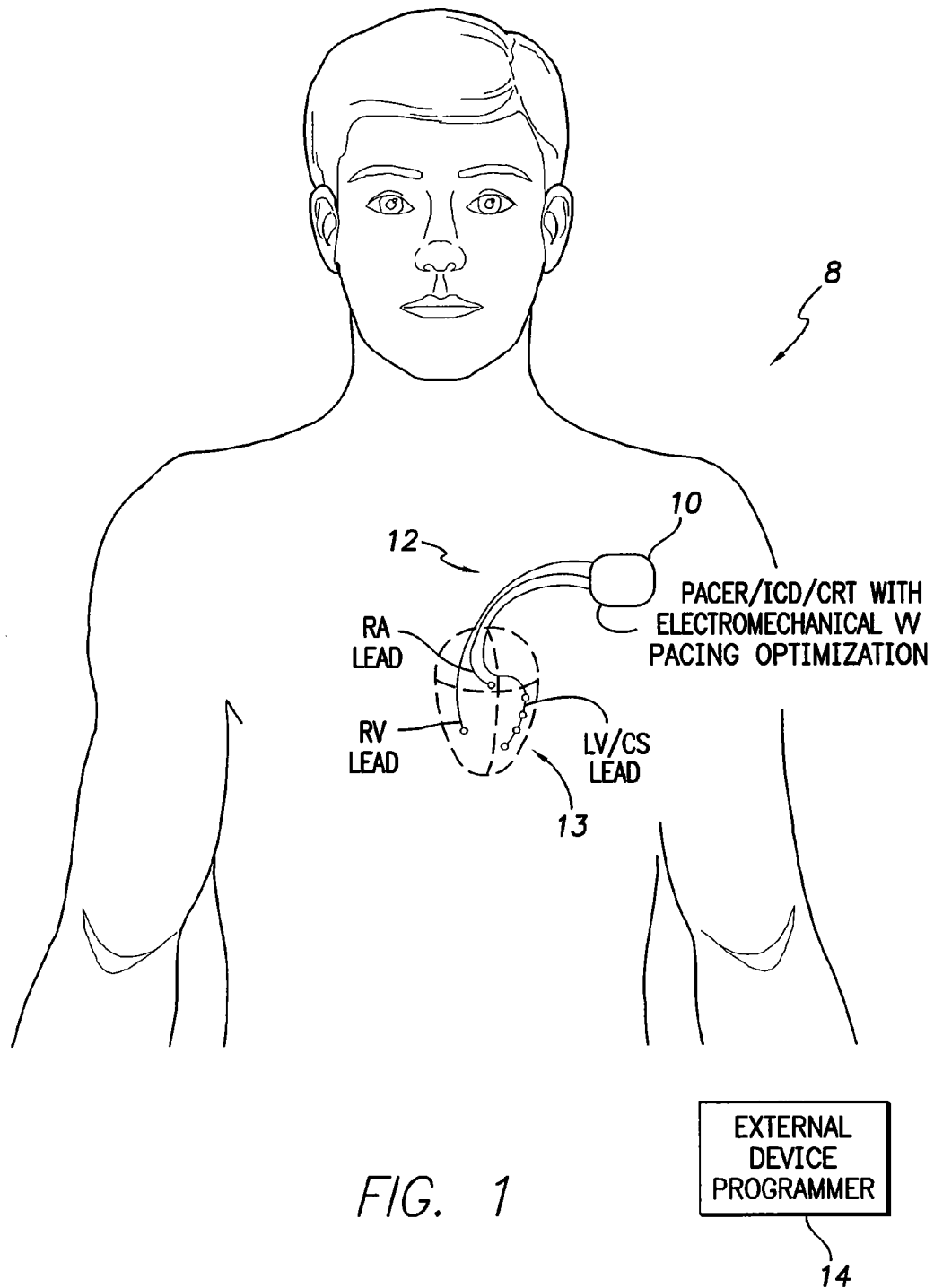
FIG. 1 illustrates pertinent components of an implantable medical system having a pacemaker, ICD or CRT device equipped to optimize VV pacing delays based on certain electromechanical delays derived from electrocardiac and cardiomechanical signals.

FIG. 1 illustrates an implantable cardiac rhythm management system 8 capable of performing rapid optimization of VV pacing delays, alone or in combination with an external programmer 14. The implantable medical system 8 includes a pacer/ICD/CRT device 10 or other cardiac rhythm management device equipped with one or more leads 12 implanted on or within the heart of the patient, including a multi-pole LV lead implanted via the coronary sinus (CS). In FIG. 1, a stylized representation of the set of leads is provided. To illustrate the multi-pole configuration of the LV lead, a set of electrodes 13 is shown distributed along the LV lead. The RV and RA leads are each shown with a single electrode, though each of those leads may include additional electrodes as well, such as tip/ring electrode pairs. Still further, the LV lead can also include one or more left atrial (LA) electrodes mounted on or in the LA via the CS. See FIG. 11 for a more complete and accurate illustration of various exemplary leads, including an exemplary multi-pole LV lead. It is noted that a multi-pole lead is not required though such a lead provides advantages in terms of pacing/sensing vector selection.

Figure 2:
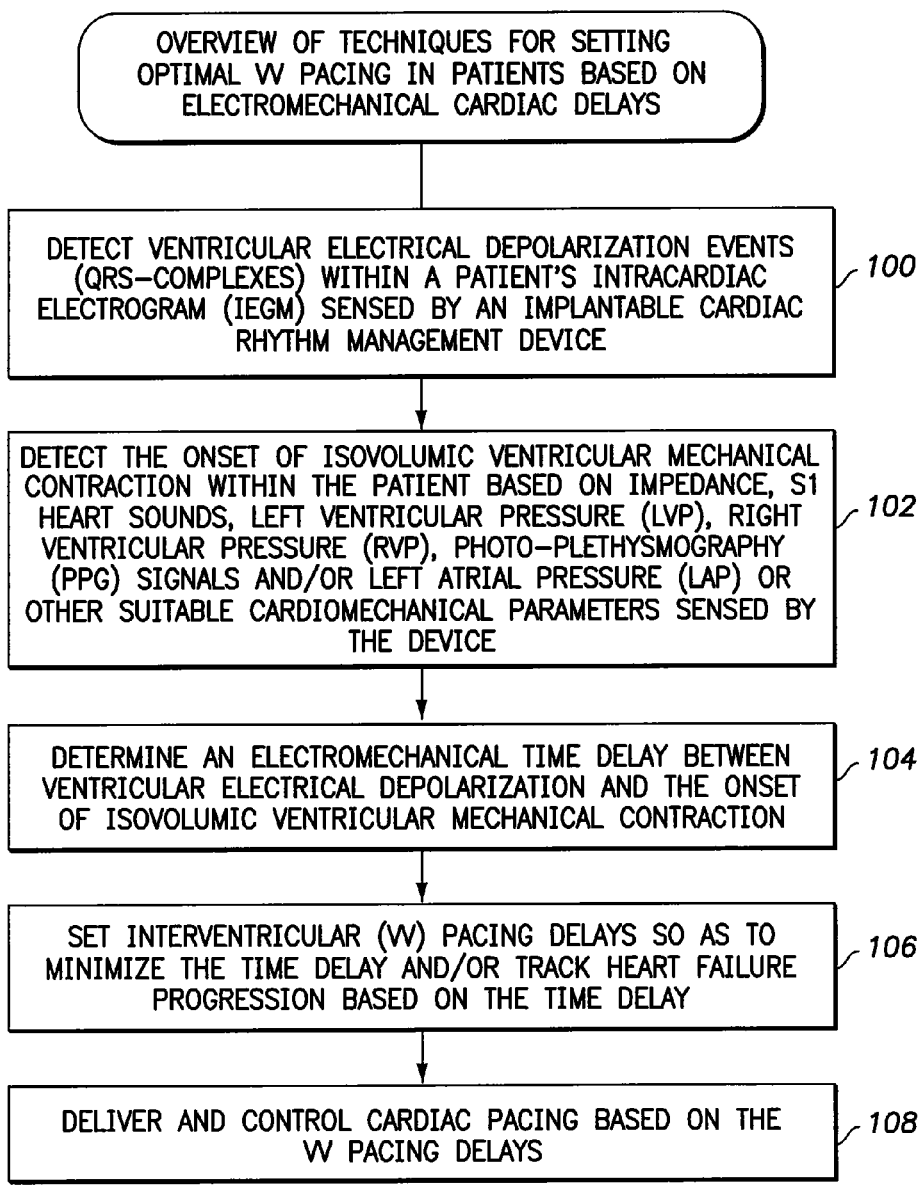
FIG. 2 is a flowchart providing an overview of a technique for setting preferred or optimal VV pacing delays that may be performed by the system of FIG. 1.

FIG. 2 broadly summarizes a general technique for optimizing VV pacing delays that can be exploited by the components of FIG. 1. Beginning at step 100, ventricular electrical depolarization events (QRS-complexes) are detected within a patient IEGM sensed by the implantable device. At step 102, the onset of isovolumic ventricular mechanical contraction is detected within the patient based on impedance, S1 heart sounds, LVP, RVP, PPG signals and/or LAP or other suitable cardiomechanical signal parameters sensed by the device. Various exemplary techniques for detecting the onset of isovolumic contraction will be described in detail below. At step 104, an electromechanical time delay between ventricular electrical depolarization (preferably the peak of the QRS complex) and the onset of isovolumic ventricular mechanical contraction is determined. Herein, this electromechanical time delay is referred to as T_QtoVC. At step 106, preferred or optimal VV pacing delays are set so as to minimize T_QtoVC. Additionally or alternatively, the electromechanical time delay may be used to monitor, track or trend heart failure within the patient. In this regard, a significant change in T_QtoVC may be indicative of a significant change in heart failure within the patient. Typically, an increase over time in the T_QtoVC value is indicative of progression or worsening of heart failure within the patient. Then, at step 108, cardiac pacing is delivered and/or controlled based on the VV pacing delays. Thus, FIG. 2 broadly summarizes a T_QtoVC-based VV optimization technique. In some examples, this optimization procedure is used in conjunction with IEGM-based VV optimization techniques, such as QuickOpt™. In other examples, the T_QtoVC-based VV optimization is used as a standalone technique.

Whether 'standalone' or 'combined', the optimization can be performed under the control of a clinician operating an external programmer, with the clinician reviewing data received from the implanted device and controlling any reprogramming thereof. For example, the external programmer can process IEGM and impedance data received from the implanted device to determine and recommend optimal VV pacing delays, which are then programmed into the implanted device via telemetry under clinician control. In some implementations, the implanted device itself performs the VV optimization and then reprograms its own VV delays accordingly. That is, some or all of the steps of FIG. 2 can be performed by the implantable device itself, if so equipped.

Note also that other external devices beside a device programmer can be used to perform the VV optimization, such as bedside monitors or the like. In some embodiments, systems or devices such as the HouseCall™ system or the Merlin@home/Merlin.Net systems of St. Jude Medical are used.

Standalone Electromechanical Delay-Based VV Pacing Optimization Examples

Figure 3:
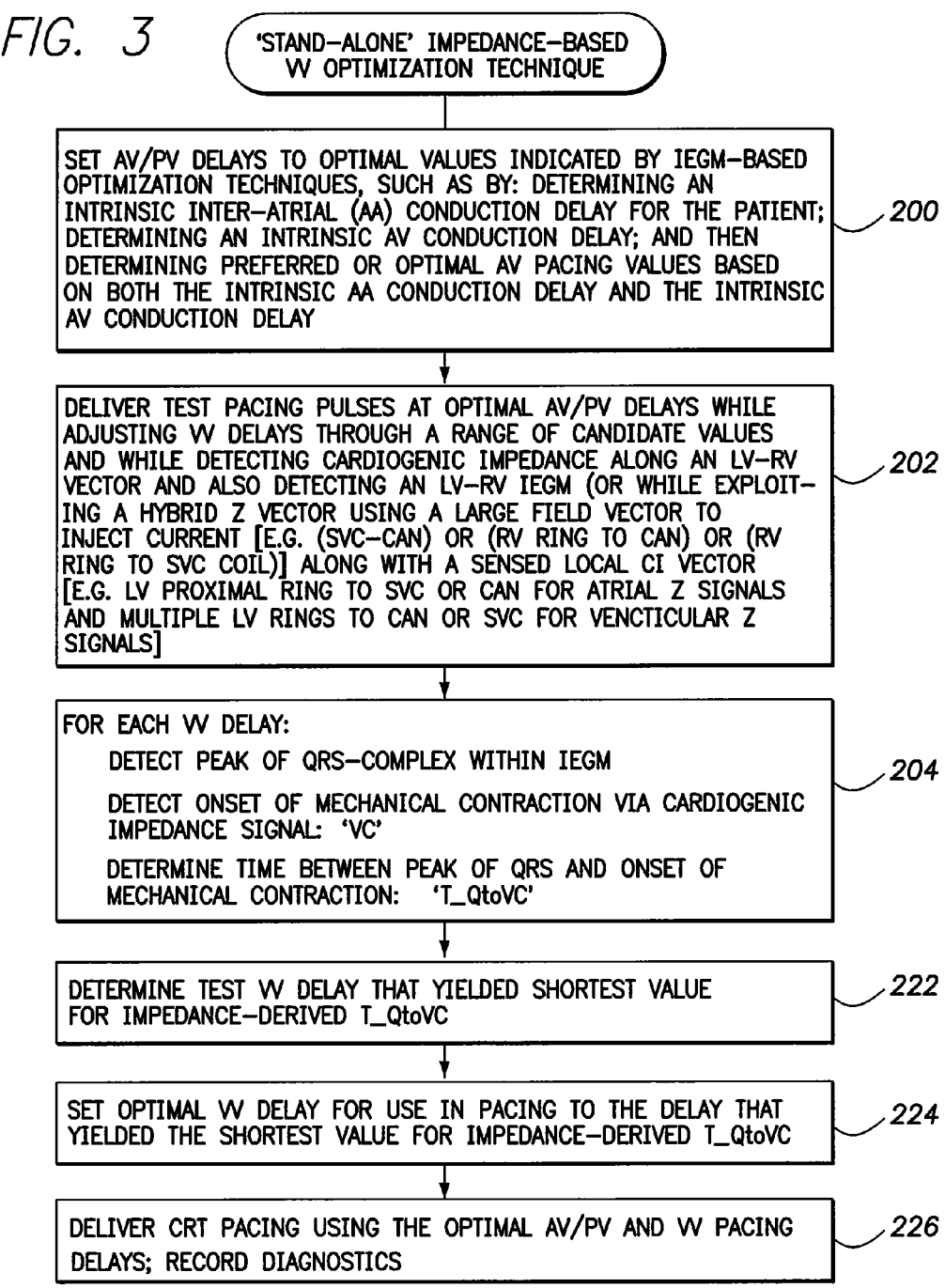
FIG. 3 is a flowchart illustrating an exemplary 'standalone' implementation of the technique of FIG. 2 wherein impedance signals are exploited, in part, to assess electromechanical delays (e.g. T_QtoVC delays)

FIG. 3 illustrates a first standalone optimization example, wherein cardiogenic impedance is exploited along with IEGM signals to assess T_QtoVC. Beginning at step 200, the device sets AV/PV pacing delays to preferred or optimal values indicated by QuickOpt or other suitable IEGM-based AV/PV optimization techniques. QuickOpt techniques are described in several of the patent documents cited above, such as in U.S. Pat. No. 7,248,925, which is incorporated by reference herein in its entirety. Briefly, in one example, both an intrinsic inter-atrial AA conduction delay and an intrinsic AV conduction delay are determined for the patient. Then, the preferred AV delay for use with the patient is determined based on the intrinsic AA conduction delay in combination with the intrinsic AV conduction delay. Additionally or alternatively, electromechanical-based AV/PV pacing delay optimization techniques can be used as described in [co-pending] U.S. patent application Ser. No. 12/957,142 of Min, filed Nov. 30, 2010, entitled "Systems and Methods for Determining Optimal Atrioventricular Pacing Delays based on Electromechanical Delays".

At step 202, the device delivers a set of test pacing pulses at the optimal AV/PV delays while adjusting VV delays through a range of permissible candidate values and while detecting cardiogenic impedance (Z) along an LV-RV vector (as well as detecting an LV-RV IEGM signal.) A particularly effective tri-phasic impedance detection pulse for use in detecting cardiogenic impedance is described in U.S. patent application Ser. No. 11/558,194 of Panescu et al., entitled "Closed-Loop Adaptive Adjustment of Pacing Therapy based on Cardiogenic Impedance Signals Detected by an Implantable Medical Device." However, other impedance detection pulses or waveforms may instead be exploited.

Additionally or alternatively, the device can exploit a hybrid vector such as a large field vector to inject current [e.g. (SVC-can) or (RV ring to can) or (RV ring to SVC coil)] along with a sensed local cardiogenic impedance (CI) vector [e.g. LV proximal ring to SVC or can for atrial Z signals and multiple LV rings to can or SVC for ventricular Z signals].)

Note also that, rather than detecting impedance, other related electrical signals or parameters can instead be exploited, such as admittance, conductance, immittance or their equivalents. This depends, in part, on how these parameters are defined. Impedance is the numerical reciprocal of admittance. Conductance is the numerical reciprocal of resistance. In general, impedance and admittance are vector quantities, which may be represented by complex numbers (having real and imaginary components.) The real component of impedance is resistance. The real component of admittance is conductance. When exploiting the real components of these values, conductance can be regarded as the reciprocal of impedance. Likewise, when exploiting the real components, admittance can be regarded as the reciprocal of resistance. Immittance represents either impedance or admittance. Generally, herein, "impedance signals" broadly encompasses impedance and/or any of these electrical equivalents and those skilled in the art can readily covert one such parameter to another.

At step 204, for each candidate VV delay within the range of permissible values, the device detects the peak of the corresponding QRS-complex within the IEGM. (The peak is preferred since it is easy to detect but other features of the QRS complex could be used in other implementations.) The device also tracks dZ/dt and detects the onset or beginning of isovolumic ventricular contraction (denoted herein as 'VC'.) In some patients, VC can correspond with max($dZ^2/dt^2$.) Still further, at step 204, the device determines or measures a time delay between the peak of the QRS and the onset of isovolumic ventricular contraction (denoted herein as 'T_QtoVC'.)

Figure 4:
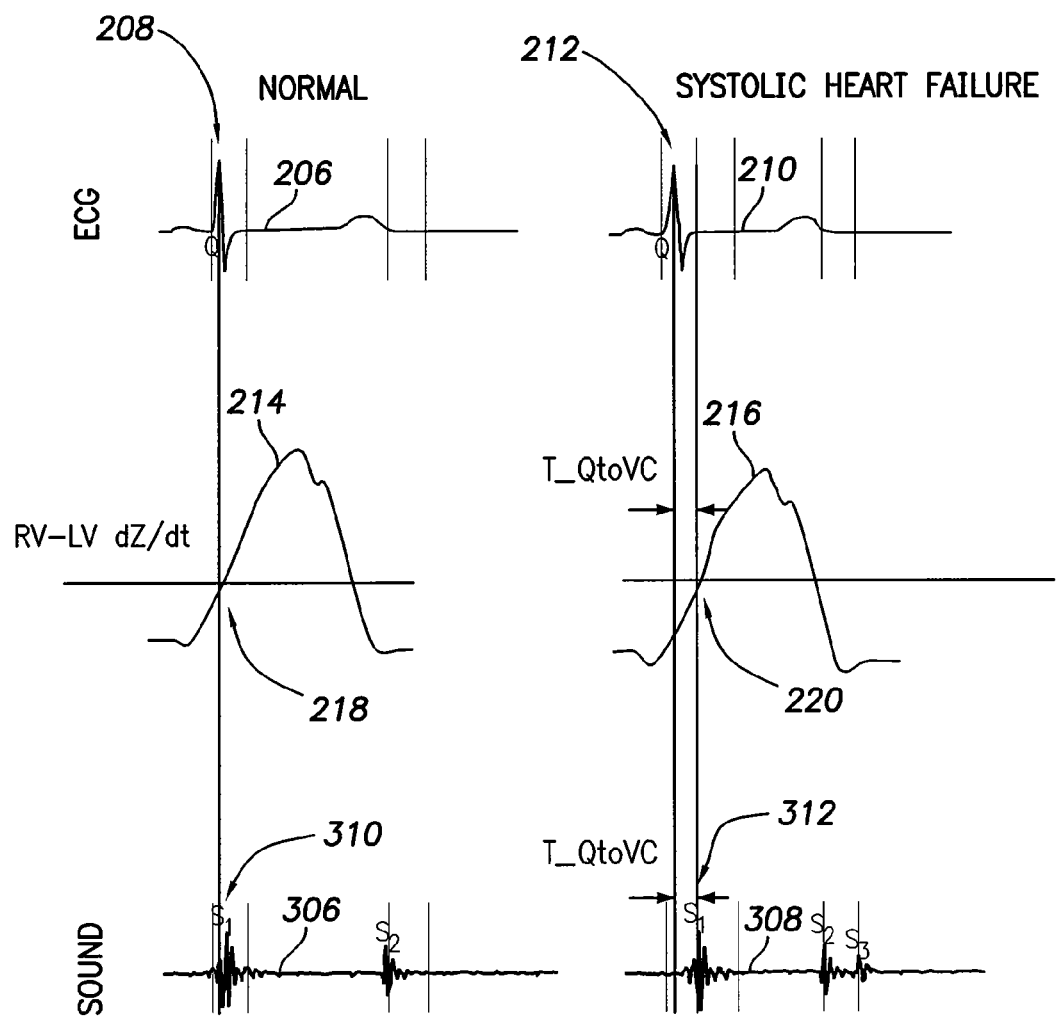
FIG. 4 is a graph illustrating exemplary electrocardiac signals, impedance signals and heart sound signals for both normal and systolic heart failure patients, and particularly illustrating a T_QtoVC delay exploited by the technique of FIG. 3.

FIG. 4 illustrates an exemplary electrical cardiac signal 206 with a QRS complex 208 for a normal patient, as well as an exemplary cardiac signal 210 with a QRS complex 212 for a patient with systolic heart failure. Corresponding dZ/dt signals 214 and 216 are shown for normal and heart failure patients, with the onset of isovolumic mechanical contraction identified in each, 218 and 220, respectively. The time delay T_QtoVC is specifically illustrated in the systolic heart failure example. No significant T_QtoVC delay appears for the normal example. That is, in the normal (i.e. healthy) patients, the QRS triggers a prompt mechanical contraction of the ventricles such that T_QtoVC is small or substantially near zero. However, in failing hearts, there can be a greater delay between the QRS and the onset of isovolumic mechanical contraction, resulting in T_QtoVC no longer being small or zero. In particular, it is hypothesized that when a narrow QRS complex is caused by lines of functional blocks (as can occur in CRT nonresponders), T_QtoVC is no longer near zero. Accordingly, VV delays can be optimized, particularly for use with patients who might otherwise be regarded as CRT nonresponders, so as to reduce T_QtoVC within their hearts.

Note that FIG. 4 also shows heart sounds, which will be discussed below. Note also that, insofar as the cardiac signal traces of FIG. 4 are concerned, the traces are of surface electrocardiogram (ECG) signals, rather than internal IEGMs as would be detected by a pacer/ICD. However, the timing of the peaks of ECGs (including both real ECGs and pseudo-ECGs) and IEGMs are substantially similar and both can exhibit a sharp QRS peak, as shown.

Returning to FIG. 3, at step 222, the device determines the test VV delay that yields the shortest or smallest value for the impedance-derived T_QtoVC. This is deemed to be the preferred or optimal VV delay for the patient. It should be understood that the optimal pacing delays described herein are not necessarily absolutely optimal in a given quantifiable or mathematical sense. As can be appreciated, what constitutes an "optimal" pacing delay depends on the criteria used for judging the resulting performance, which can be subjective in the minds of some clinicians. The pacing delays determined by the techniques described herein represent, at least, "preferred" configurations. Clinicians may choose to adjust or alter the selection via device programming for particular patients, at their discretion.

At step 224, the device sets the optimal VV delay for use in pacing the patient to the delay that yielded the shortest value of the impedance-derived T_QtoVC. (As will be described below with reference to FIG. 9, this shortest delay value can also be compared against a threshold to identify CRT nonresponders.) At step 226, the device delivers cardiac pacing using the optimal AV/PV (from step 200) and the optimal VV pacing delay (from step 222.) Additionally, suitable diagnostic information can be stored, such as data pertaining to the various candidate VV delays that have been tested, the resulting T_QtoVC delay values, as well as the current AV/PV delays in use.

Figure 5:
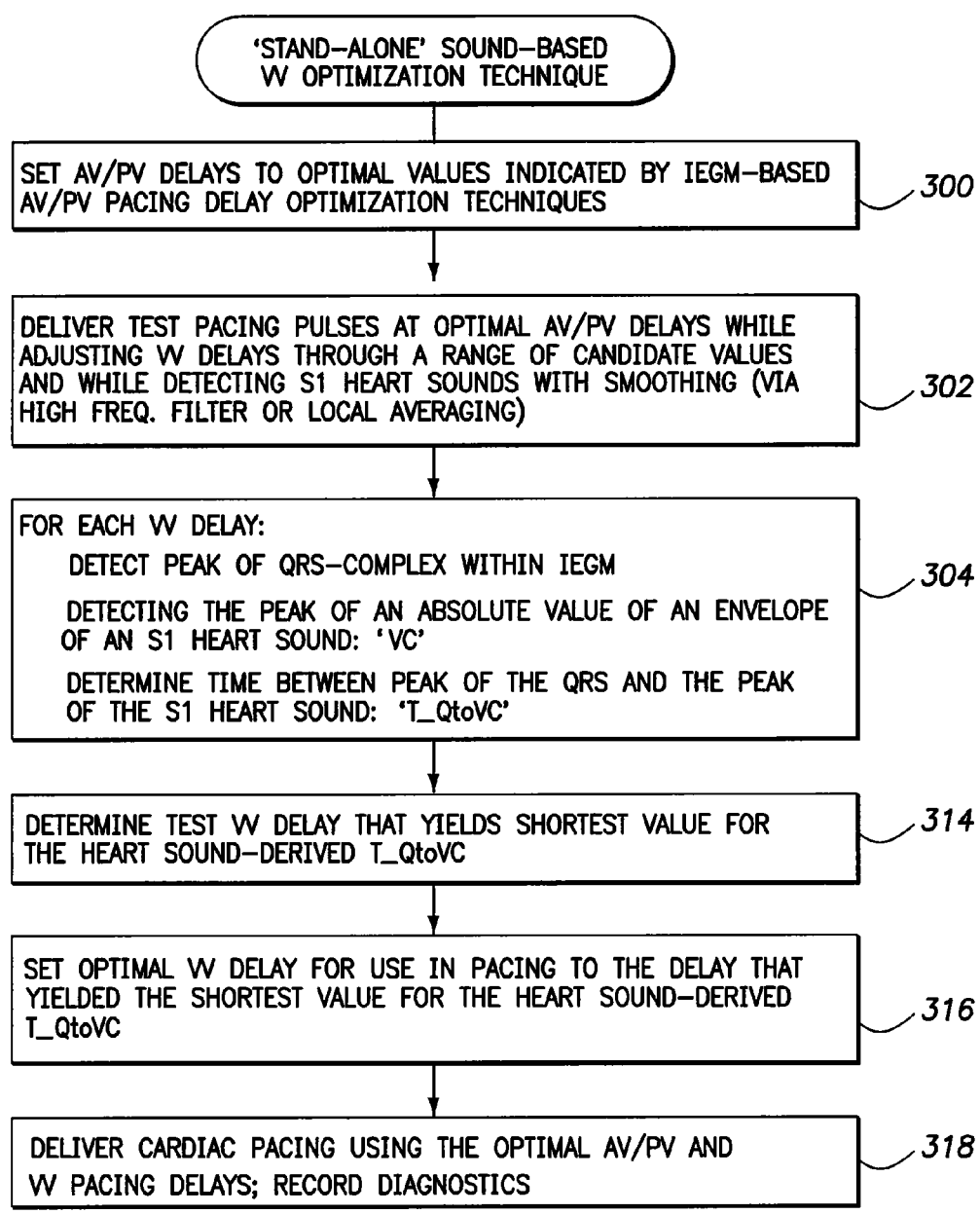
FIG. 5 is a flowchart illustrating another exemplary 'standalone' implementation of the technique of FIG. 2 wherein S1 heart sound signals are exploited, in part, to assess T_QtoVC delays.

Turning now to FIG. 5, another standalone example is provided, wherein heart sounds are used by the device. Many of the steps are similar to those of FIG. 3 and hence will not be described in detail again. Briefly, at step 300, the device sets AV/PV delays to optimal values and, at step 302, delivers test pacing pulses while adjusting VV delays through a range of permissible candidate values and while detecting heart sounds, particularly the peak of the absolute value of an envelope of the S1 heart sound. Techniques for detecting heart sounds are discussed, e.g., in U.S. Pat. No. 7,139,609 to Min, et al., entitled "System and Method for Monitoring Cardiac Function via Cardiac Sounds using an Implantable Cardiac Stimulation Device." See, also, U.S. Pat. No. 6,477,406 to Turcott, entitled "Extravascular Hemodynamic Acoustic Sensor." At step 304, for each candidate VV delay, the device detects the peak of the QRS of the IEGM and the peak in an S1 heart sound, which is deemed to correspond to the onset of isovolumic ventricular contraction. (Note that the raw S1 sound can be processed over a local smoothing scheme before locating the peak S1. The smoothing can be done by filtering a high frequency component or by local averaging over neighbors.) At step 304, the device also determines or measures the time delay between the peak of the QRS and the peak of S1. (This delay is again denoted as 'T_QtoVC'.) Exemplary heart sound signals 306 and 308 are shown in FIG. 4 for the normal patient and the systolic heart failure patient. The peak of the S1 heart sound is identified in each trace, 310 and 312, respectively. As can be seen, time delay T_QtoVC corresponds to the delay between the peak of the QRS and the peak of S1.

At step 314 of FIG. 5, the device determines the VV delay that yielded the shortest or smallest value for the heart sound-derived T_QtoVC, which is deemed to be the preferred or optimal VV delay for the patient. At step 316, the device sets the optimal VV delay to the delay that yielded the shortest value of the heart sound-derived T_QtoVC and, at step 318, delivers cardiac pacing using the optimal AV/PV and the optimal VV pacing delay. Additionally, suitable diagnostic information can again be stored.

Figure 6:
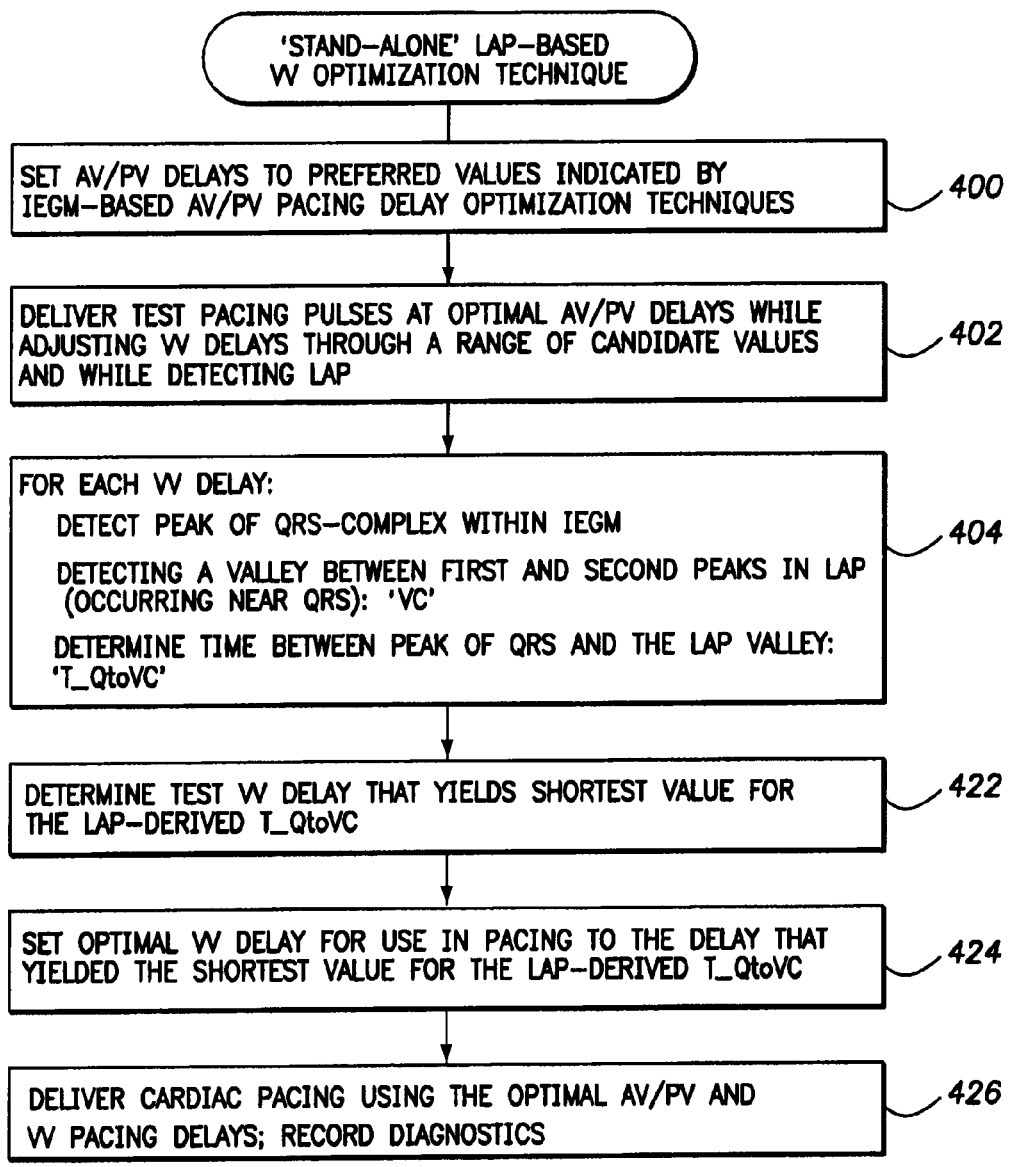
FIG. 6 is a flowchart illustrating yet another exemplary 'standalone' implementation of the technique of FIG. 2 wherein LAP signals are exploited, in part, to assess T_QtoVC delays.

FIG. 6 illustrates yet another standalone example, wherein LAP is used by the device. Again, many of the steps are similar to those of FIG. 3 and will not be described in further detail. Briefly, at step 400, the device sets AV/PV delays to optimal values and, at step 402, delivers test pacing pulses while adjusting VV delays and while detecting LAP. LAP sensors are discussed in, for example, U.S. Published Patent Application 2003/0055345 of Eigler et al., entitled "Permanently Implantable System and Method for Detecting, Diagnosing and Treating Congestive Heart Failure." Techniques for detecting LAP that do not necessarily require an LAP sensor are discussed in U.S. Provisional Patent Application No. 60/787,884 of Wong et al., entitled, "Tissue Characterization Using Intracardiac Impedances with an Implantable Lead System," filed Mar. 31, 2006 and U.S. patent application Ser. No. 11/558,101 of Panescu et al., entitled "Systems and Methods to Monitor and Treat Heart Failure Conditions."

At step 304, for each candidate VV delay, the device detects the peak of the QRS of the IEGM within each cardiac cycle and a valley between first and second peaks in the LAP signal (that occur contemporaneously with, or just following, the QRS of the cardiac cycle.) This first valley is deemed to correspond to the onset of isovolumic ventricular contraction within the cardiac cycle. At step 404, the device also determines or measures the time delay between the peak of the QRS and the valley in LAP. (This delay is again denoted as 'T_QtoVC'.)

Figure 7:
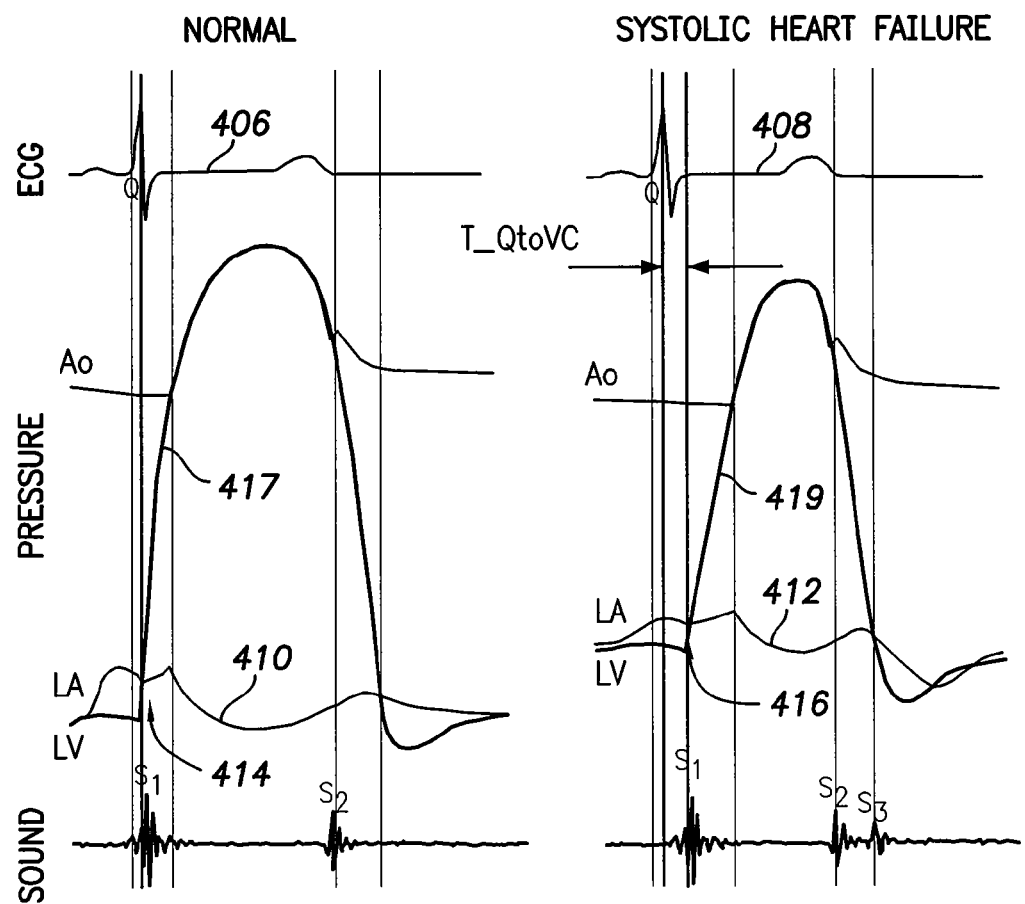
FIG. 7 is a graph illustrating exemplary electrocardiac signals, cardiac pressure signals and S1 heart sound signals for both normal and systolic heart failure patients, and particularly illustrating an LAP signal exploited by the technique of FIG. 6.

FIG. 7 illustrates electrical cardiac signals for a single cardiac cycle for normal and heart failure patients, 406 and 408, as well as corresponding LAP signals, 410 and 412. LAP signals have two peaks near the QRS or S1 sound. The second peak is aligned with opening of Ao valve and the valley between the two peaks (which is the "first valley" following the QRS) is associated with the onset of isovolumic contraction of both normal and HF patients. The first valley within the normal LAP is denoted 414; the first valley within the heart failure LAP is denoted 416. The time delay T_QtoVC is illustrated in the heart failure example. Note that the figure also shows heart sounds and LVP for the normal patient, 417, and the heart failure patient, 419. Heart sounds were discussed above. LVP is discussed below.

Figure 8:
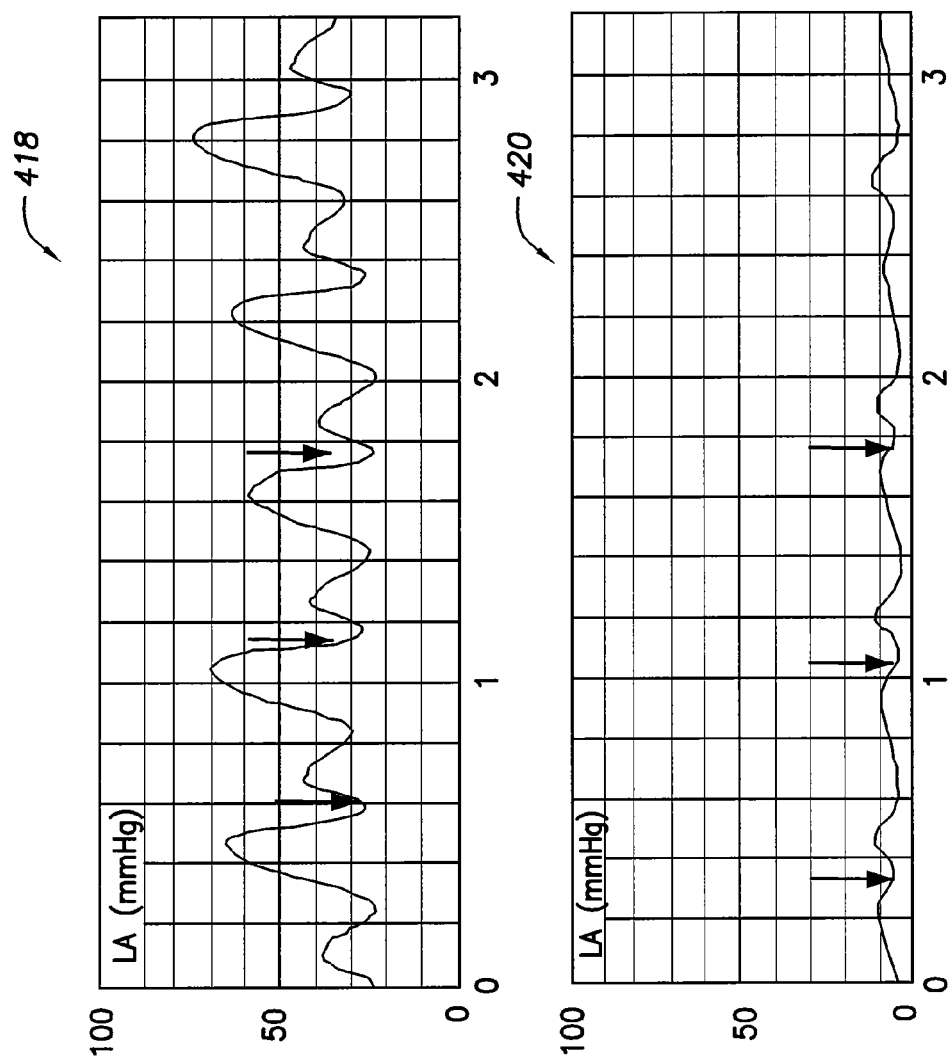
FIG. 8 is a graph illustrating additional exemplary LAP signals that can be exploited by the technique of FIG. 6.

FIG. 8 illustrates exemplary LAP traces derived using St Jude Medical's Heart PAD system over several cardiac cycles (wherein the Heart PAD system is a subcutaneous (subQ) device with an LAP sensor implanted at the intra-atrial septum.) Two such LAP traces are shown, 418, 420, for different patients having significantly different peak LAP values. Various valleys and peaks appear in both of the traces. P-wave or QRS landmarks can be identified within a corresponding IEGM (not shown in FIG. 7) for use in identifying the "first valley" associated with isovolumic contraction within each cardiac cycle. Additionally, or alternatively, the peak of the S1 heart sound (assuming it has been detected) can be used to identify these valleys. Within FIG. 8, arrows denote these valleys within several consecutive cardiac cycles.

Returning to FIG. 6, the device at step 422 determines the VV delay that yielded the shortest or smallest value for the LAP-derived T_QtoVC, which is deemed to be the preferred or optimal VV delay for the patient. At step 424, the device sets the optimal VV delay to the delay that yielded the shortest value of the LAP-derived T_QtoVC and, at step 426, delivers cardiac pacing using the optimal AV/PV and the optimal VV pacing delay. Suitable diagnostic information can again be stored.

Thus, FIGS. 3-8 illustrate various exemplary 'standalone' techniques for optimizing VV pacing delays that exploit impedance, heart sounds or LAP. Similar standalone techniques can be applied for optimizing VV delays that use LVP, RVP, PPG signals or other appropriate cardiomechanical signals. For example, the onset of isovolumic contraction can be identified within LVP based on the timing of a sharp increase in LVP (see LVP traces 417 and 419 of FIG. 7) and then used to determine T_QtoVC. Similarly, sharp increases in RVP and/or PPG signals can be used to detect the onset of isovolumic contraction. Hence, various cardiomechanical signals can be exploited in accordance with the principles of the invention to determine T_QtoVC for use in optimizing VV pacing delays. Based on the teachings and guidance provided herein, those skilled in the art can identify particular features of these or other cardiomechanical signals that serve to detect the onset of isovolumic ventricular contraction.

Depending upon the particular implementation, some or all of the steps of these figures are performed by the implantable device itself. Additionally or alternatively, at least some of the steps can be performed by an external programmer or other external system.

Combined VV Optimization Example

Figure 9:
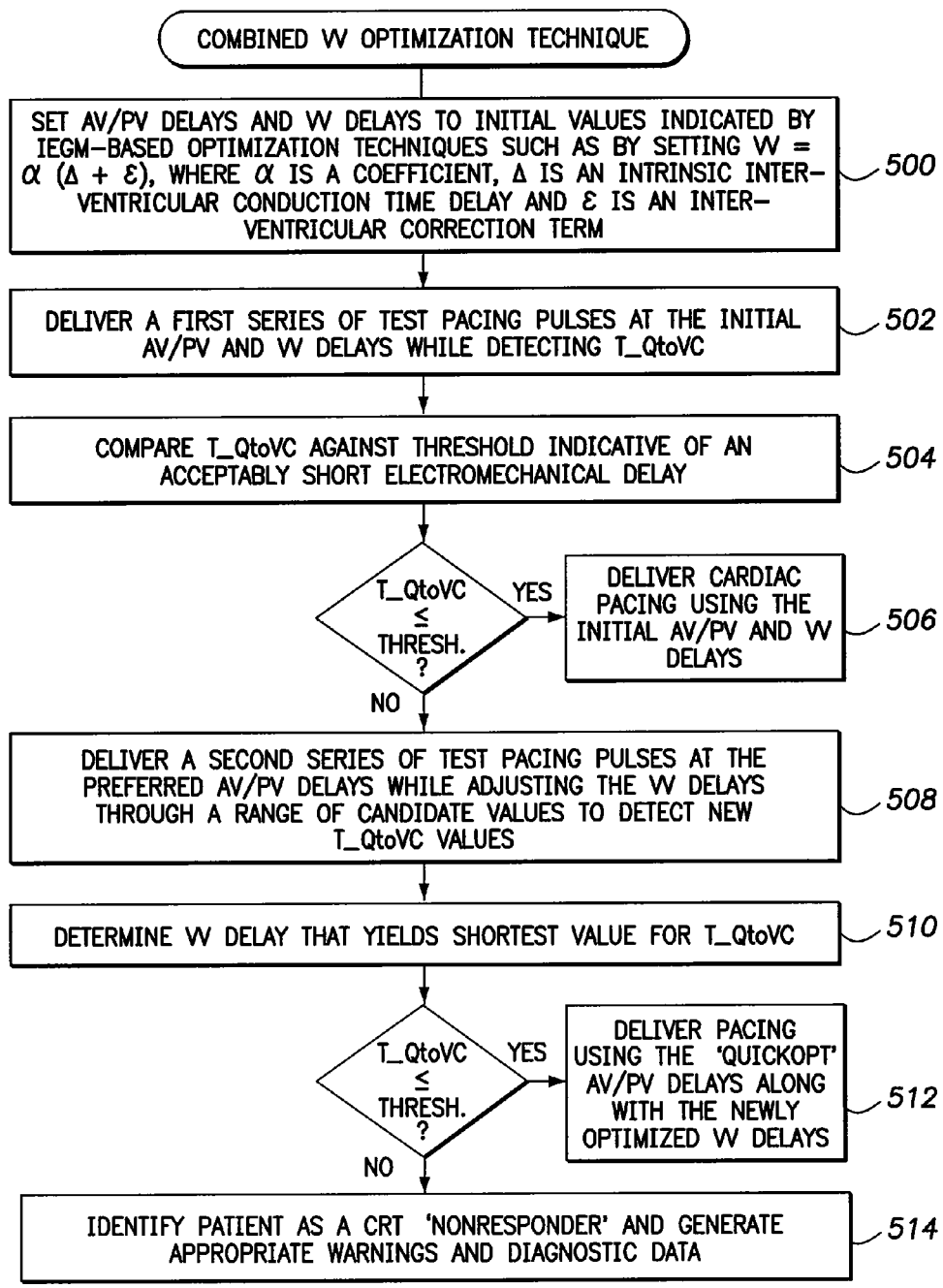
FIG. 9 is a flowchart illustrating an exemplary 'combined' implementation of the technique of FIG. 2 that exploits both IEGM-based VV optimization as well as T_QtoVC-based optimization, and which also identifies CRT nonresponders.

FIG. 9 provides an example of a 'combined' technique that optimizes VV pacing delays by exploiting both IEGM-based VV optimization and the aforementioned T_QtoVC-based optimization. This technique also identifies possible CRT nonresponders. Beginning at step 500, the device sets AV/PV pacing delays and VV pacing delays to initial values as indicated by QuickOpt or other suitable IEGM-based AV/PV/VV optimization techniques. Briefly, in one example, a first preferred VV delay is set using: VV=$\alpha$ ($\Delta$+$\epsilon$), where $\alpha$ is a coefficient, $\Delta$ is an intrinsic interventricular conduction time delay and $\epsilon$ is an interventricular correction term. Again, see the QuickOpt techniques described in the various patent documents cited above, particularly U.S. patent application Ser. No. 12/639,881, filed Dec. 16, 2009, which is incorporated by reference herein.

At step 502, the device delivers a first set of test pacing pulses at the initial AV/PV and VV delays while detecting T_QtoVC using any of the determination techniques discussed herein. At step 504, the device compares T_QtoVC against a predetermined threshold indicative of an acceptable electromechanical delay. If the value for T_QtoVC obtained using the initial AV/PV/VV values is acceptable (i.e. T_QtoVC≤Threshold) then, at step 506, the device delivers cardiac pacing using the initial AV/PV and VV delays (i.e. the delays obtained at step 500 using the IEGM-based optimization techniques.) A suitable value for the threshold may be programmed in advance by the clinician or determined based on otherwise routine studies of acceptable electromechanical delays for patients.

If, however, the value for T_QtoVC obtained using the initial AV/PV/VV values (e.g. IEGM-based pacing delay values) is not acceptable (T_QtoVC>Threshold) then additional optimization steps are performed. At step 508, the device deliver a second series of test pacing pulses at the preferred AV/PV delays while adjusting the VV delays through a range of candidate values to detect new T_QtoVC values. At step 510, the device determines the VV delay that yields the shortest value for T_QtoVC. This may be accomplished using the techniques described above. This shortest value for T_QtoVC is then compared against the threshold indicative of an acceptable electromechanical delay. If the newly optimized value for T_QtoVC is found to be acceptable (i.e. T_QtoVC≤Threshold) then, at step 512, the device delivers cardiac pacing using the initial AV/PV delays (determined at step 500) along with the new VV value (determined at step 510.) However, if the new value for T_QtoVC is still not acceptable (T_QtoVC>Threshold) then the patient is identified as a possible CRT nonresponder, at step 514, and appropriate warnings and diagnostic data are generated. Such data can specify the shortest T_QtoVC that had been found and the VV value used to obtain that T_QtoVC value. Note that if a patient is identified as a possible nonresponder, it might be possible to adjust the location of the electrodes to improve pacing so that the patient is no longer a nonresponder, which is discussed in the next section.

Electrode Position/Vector Optimization Example

Figure 10:
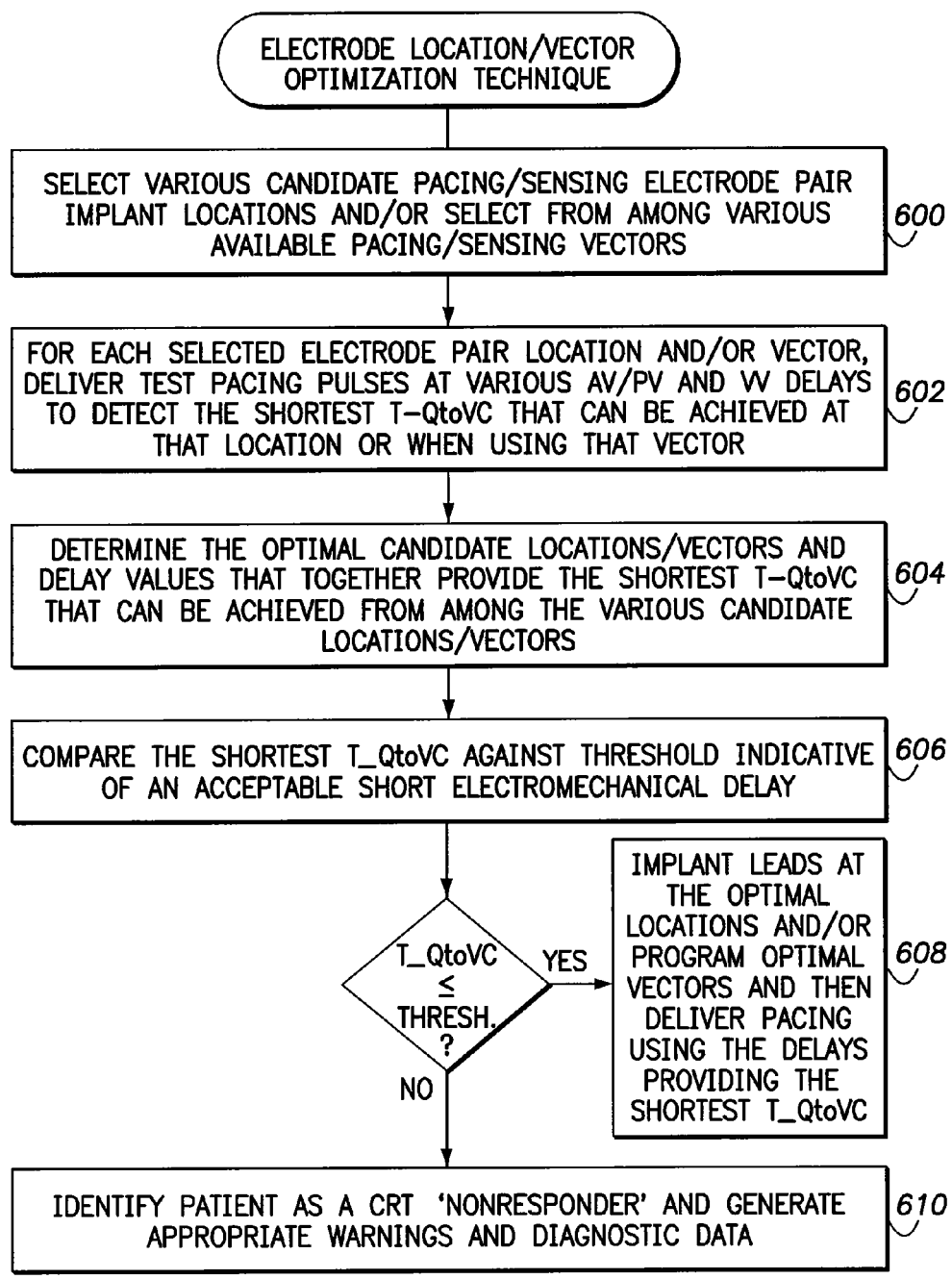
FIG. 10 is a flowchart illustrating an exemplary electrode placement optimization technique, which may be used to optimize selection/positioning of the vectors/leads of the device of FIG. 1.

FIG. 10 provides an example of a technique that optimizes the implant location of electrodes used for ventricular pacing (or optimizes the selection of particular pacing/sensing vectors from among various candidate vectors.) This technique also identifies CRT nonresponders. At step 600, various candidate pacing/sensing electrode pair implant locations are selected (and/or various available pacing/sensing vectors are selected.) For example, if the lead system has not yet been implanted, then various implant locations can be selected for testing. If the lead system has already been implanted (and assuming it accommodates various programmable pacing/sensing vectors), then various particular vectors are selected for testing. As can be appreciated, if multi-pole leads have been implanted, numerous pacing/sensing vectors are typically available.

At step 602, for each selected electrode pair location (and/or vector), test pacing pulses are delivered at various AV/PV and VV delays to detect the shortest T_QtoVC that can be achieved at that location (or when using that vector.) In this regard, the various techniques described above with reference to FIGS. 3-8 can be used wherein VV delays are varied through a range of values while measuring T_QtoVC to identify the VV value yielding the shortest T_QtoVC value. The combined technique of FIG. 9 can also be used.

At step 604, the system determines the optimal locations/vectors and VV delay values that together provide the shortest T_QtoVC that can be achieved from among the various candidate locations/vectors. For example, if five different candidate implant locations had been selected and tested, the particular location that yielded the shortest T_QtoVC value is identified as the optimal location. As another example, if ten different candidate vectors had been selected and tested, the particular vector that yielded the shortest T_QtoVC value is identified as the optimal vector. Note that if both the location of the leads and the choice of pacing/sensing vectors are selectable (which is typically the case if the leads have not yet been implanted), then step 604 can be performed to identify the particular combination of lead implant location and pacing/sensing vector that yields the overall shortest T_QtoVC value.

It should be understood that the optimal electrode locations and/or pacing/sensing vectors identified at step 604 are not necessarily absolutely optimal in a given quantifiable or mathematical sense. As already explained, what constitutes "optimal" depends on the criteria used for judging the resulting performance, which can be subjective in the minds of some clinicians. The locations/vectors determined by the techniques described herein represent, at least, "preferred" locations/vectors. Clinicians may choose to adjust or alter the selection of the locations/vectors for particular patients, at their discretion.

At step 606, the system compares the shortest T_QtoVC obtained at step 604 against a preprogrammed threshold indicative of an acceptably short electromechanical delay, such as the threshold discussed above. If the shortest value achieved for T_QtoVC obtained is found to be acceptable (i.e. T_QtoVC≤Threshold) then, at step 608, the leads are implanted at the optimal locations (and/or the optimal vectors are programmed) and then pacing is delivered using the VV delays that provided the shortest T_QtoVC. However, if the shortest value for T_QtoVC achieved at step 604 is still not acceptable (T_QtoVC>Threshold) then the patient is identified as a CRT nonresponder, at step 610, and appropriate warnings and diagnostic data are generated. Such data can specify the various implant locations and/or vectors that had been tested and the shortest T_QtoVC obtained at each. If the patient is deemed to be a nonresponder even after various implant locations and vector combinations have been tested, then non-CRT therapies may need to be applied to the particular patient, at the discretion of the clinician.

As with the preceding embodiments, the optimization techniques of FIG. 10 are typically performed under the control of a clinician operating an external programmer. However, in implementations where leads have already been implanted and various pacing/sensing vectors are selectable by the device (as might be the case when multi-pole leads are in use), the implanted device itself can performs the optimization techniques FIG. 10 to identify a preferred vector and then reprograms its pacing/sensing vectors and VV delays accordingly. That is, some or all of the steps of FIG. 10 can be performed by the implantable device itself, if so equipped.

Although primarily described with respect to examples having a pacer/ICD equipped to deliver CRT, other implantable medical devices may be equipped to exploit the techniques described. For the sake of completeness, an exemplary pacer/ICD/CRT device will now be described, which includes components for performing the functions and steps already described.

Exemplary Pacer/ICD/CRT

Figure 11:
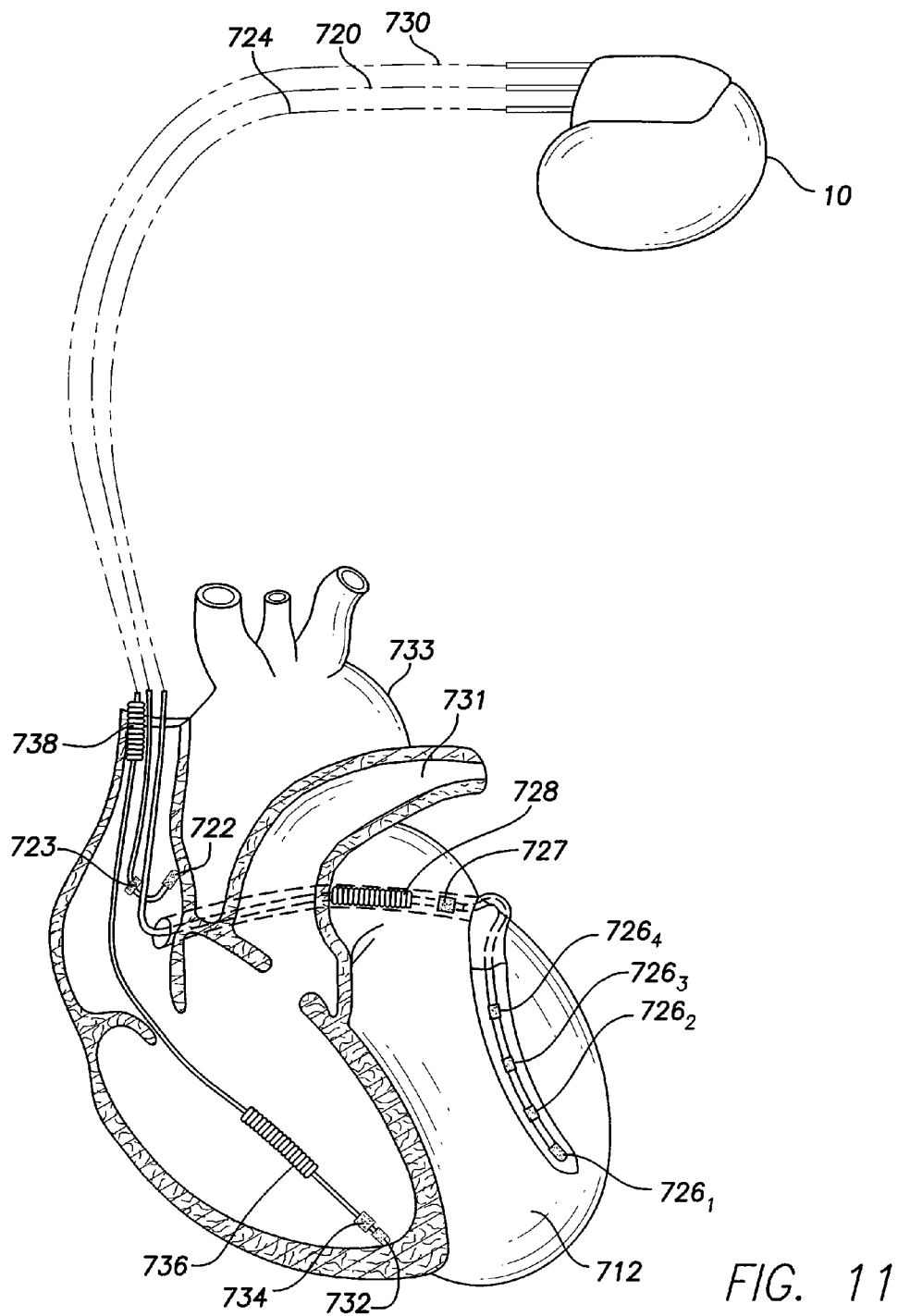
FIG. 11 is a simplified, partly cutaway view, illustrating the device of FIG. 1 along with at set of leads implanted into the heart of the patient.
Figure 12:
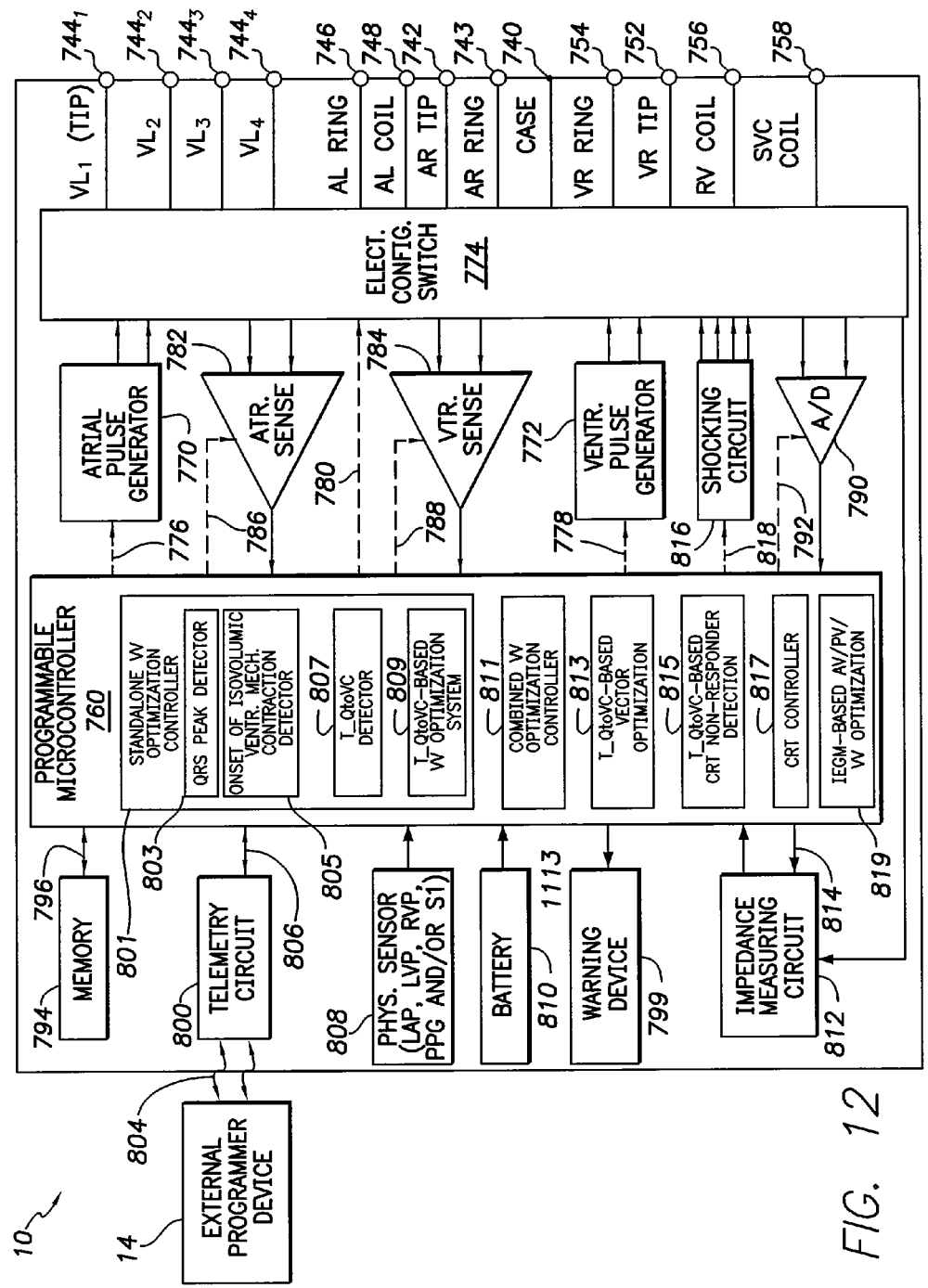
FIG. 12 is a functional block diagram of the pacer/ICD of FIG. 11, illustrating basic circuit elements that provide cardioversion, defibrillation and/or pacing stimulation in the heart an particularly illustrating on-board optimization components for performing the various optimization techniques.

With reference to FIGS. 11 and 12, a description of an exemplary pacer/ICD/CRT will now be provided. FIG. 11 provides a simplified block diagram of the device, which is a dual-chamber stimulation device capable of treating both fast and slow arrhythmias with stimulation therapy, including cardioversion, defibrillation, and pacing stimulation, and also capable of setting and using VV pacing delays, as discussed above, and delivering CRT using the VV delays. To provide other atrial chamber pacing stimulation and sensing, device 10 is shown in electrical communication with a heart 712 by way of a left atrial lead 720 having an atrial tip electrode 722 and an atrial ring electrode 723 implanted in the atrial appendage. Device 10 is also in electrical communication with the heart by way of a right ventricular lead 730 having, in this embodiment, a ventricular tip electrode 732, a right ventricular ring electrode 734, a right ventricular (RV) coil electrode 736, and a superior vena cava (SVC) coil electrode 738. Typically, the right ventricular lead 730 is transvenously inserted into the heart so as to place the RV coil electrode 736 in the right ventricular apex, and the SVC coil electrode 738 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, device 10 is coupled to a multi-pole LV lead 724 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 724 is designed to receive atrial and ventricular cardiac signals and to deliver left ventricular pacing therapy using a set of four left ventricular electrodes $726_1$, $726_2$, $726_3$, and $726_4$ (thereby providing a quadra-pole lead), left atrial pacing therapy using at least a left atrial ring electrode 727, and shocking therapy using at least a left atrial coil electrode 728. The $726_1$ LV electrode may also be referred to as a "tip" or "distal" LV electrode. The $726_4$ LV electrode may also be referred to as a "proximal" LV electrode. In other examples, more or fewer LV electrodes are provided. Although only three leads are shown in FIG. 11, it should also be understood that additional leads (with one or more pacing, sensing and/or shocking electrodes) might be used and/or additional electrodes might be provided on the leads already shown, such as additional electrodes on the RV lead.

A simplified block diagram of internal components of device 10 is shown in FIG. 9. While a particular device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 740 for device 10, shown schematically in FIG. 12, is often referred to as the "can," "case" or "case electrode" and may be programmably selected to act as the return electrode for all "unipolar" modes. The housing 740 may further be used as a return electrode alone or in combination with one or more of the coil electrodes, 728, 736 and 738, for shocking purposes. The housing 740 further includes a connector (not shown) having a plurality of terminals, 742, 743, $744_1$-$744_4$, 746, 748, 752, 754, 756 and 758 (shown schematically and, for convenience, the names of the electrodes to which they are connected are shown next to the terminals). As such, to achieve right atrial sensing and pacing, the connector includes at least a right atrial tip terminal ($A_R$ TIP) 742 adapted for connection to the atrial tip electrode 722 and a right atrial ring ($A_R$ RING) electrode 743 adapted for connection to right atrial ring electrode 723. To achieve left chamber sensing, pacing and shocking, the connector includes a left ventricular tip terminal ($VL_1$ TIP) $744_1$ and additional LV electrode terminals $744_2$-$744_4$ for the other LV electrodes of the quadra-pole LV lead.

The connector also includes a left atrial ring terminal ($A_L$ RING) 746 and a left atrial shocking terminal ($A_L$ COIL) 748, which are adapted for connection to the left atrial ring electrode 727 and the left atrial coil electrode 728, respectively. To support right chamber sensing, pacing and shocking, the connector further includes a right ventricular tip terminal ($V_R$ TIP) 752, a right ventricular ring terminal ($V_R$ RING) 754, a right ventricular shocking terminal ($V_R$ COIL) 756, and an SVC shocking terminal (SVC COIL) 758, which are adapted for connection to the right ventricular tip electrode 732, right ventricular ring electrode 734, the $V_R$ coil electrode 736, and the SVC coil electrode 738, respectively.

At the core of device 10 is a programmable microcontroller 760, which controls the various modes of stimulation therapy. As is well known in the art, the microcontroller 760 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 760 includes the ability to process or monitor input signals (data) as controlled by a program code stored in a designated block of memory. The details of the design and operation of the microcontroller 760 are not critical to the invention. Rather, any suitable microcontroller 760 may be used that carries out the functions described herein. The use of microprocessor-based control circuits for performing timing and data analysis functions are well known in the art.

As shown in FIG. 12, an atrial pulse generator 770 and a ventricular pulse generator 772 generate pacing stimulation pulses for delivery by the right atrial lead 720, the right ventricular lead 730, and/or the LV lead 724 via an electrode configuration switch 774. It is understood that in order to provide stimulation therapy in each of the four chambers of the heart, the atrial and ventricular pulse generators, 770 and 772, may include dedicated, independent pulse generators, multiplexed pulse generators or shared pulse generators. The pulse generators, 770 and 772, are controlled by the microcontroller 760 via appropriate control signals, 776 and 778, respectively, to trigger or inhibit the stimulation pulses.

The microcontroller 760 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 774 includes a plurality of switches for connecting the desired electrodes to the appropriate I/O circuits, thereby providing complete electrode programmability. Accordingly, the switch 774, in response to a control signal 780 from the microcontroller 760, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 782 and ventricular sensing circuits 784 may also be selectively coupled to the right atrial lead 720, LV lead 724, and the right ventricular lead 730, through the switch 774 for detecting the presence of cardiac activity in each of the four chambers of the heart. Accordingly, the atrial (ATR. SENSE) and ventricular (VTR. SENSE) sensing circuits, 782 and 784, may include dedicated sense amplifiers, multiplexed amplifiers or shared amplifiers. The switch 774 determines the "sensing polarity" of the cardiac signal by selectively closing the appropriate switches, as is also known in the art. In this way, the clinician may program the sensing polarity independent of the stimulation polarity. Each sensing circuit, 782 and 784, preferably employs one or more low power, precision amplifiers with programmable gain and/or automatic gain control, bandpass filtering, and a threshold detection circuit, as known in the art, to selectively sense the cardiac signal of interest. The automatic gain control enables device 10 to deal effectively with the difficult problem of sensing the low amplitude signal characteristics of atrial or ventricular fibrillation. The outputs of the atrial and ventricular sensing circuits, 782 and 784, are connected to the microcontroller 760 which, in turn, are able to trigger or inhibit the atrial and ventricular pulse generators, 770 and 772, respectively, in a demand fashion in response to the absence or presence of cardiac activity in the appropriate chambers of the heart.

For arrhythmia detection, device 10 utilizes the atrial and ventricular sensing circuits, 782 and 784, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 760 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 790. The data acquisition system 790 is configured to acquire intracardiac electrogram signals, convert the raw analog data into a digital signal, and store the digital signals for later processing and/or telemetric transmission to an external device 802. The data acquisition system 790 is coupled to the right atrial lead 720, the LV lead 724, and the right ventricular lead 730 through the switch 774 to sample cardiac signals across any pair of desired electrodes. The microcontroller 760 is further coupled to a memory 794 by a suitable data/address bus 796, wherein the programmable operating parameters used by the microcontroller 760 are stored and modified, as required, in order to customize the operation of device 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable device 10 may be non-invasively programmed into the memory 794 through a telemetry circuit 800 in telemetric communication with the external device 802, such as a programmer, transtelephonic transceiver or a diagnostic system analyzer. The telemetry circuit 800 is activated by the microcontroller by a control signal 806. The telemetry circuit 800 advantageously allows intracardiac electrograms and status information relating to the operation of device 10 (as contained in the microcontroller 760 or memory 794) to be sent to the external device 802 through an established communication link 804. Device 10 further includes an accelerometer or other physiologic sensor 808, commonly referred to as a "rate-responsive" sensor because it is typically used to adjust pacing stimulation rate according to the exercise state of the patient. However, the physiological sensor 808 may further be used to detect changes in cardiac output, changes in the physiological condition of the heart, or diurnal changes in activity (e.g., detecting sleep and wake states) and to detect arousal from sleep. Accordingly, the microcontroller 760 responds by adjusting the various pacing parameters (such as rate, AV delay, VV delay, etc.) at which the atrial and ventricular pulse generators, 770 and 772, generate stimulation pulses. While shown as being included within device 10, it is to be understood that the physiologic sensor 808 may also be external to device 10, yet still be implanted within or carried by the patient. A common type of rate responsive sensor is an activity sensor incorporating an accelerometer or a piezoelectric crystal, which is mounted within the housing 740 of device 10. Other types of physiologic sensors are also known, for example, sensors that sense the oxygen content of blood, respiration rate and/or minute ventilation, pH of blood, ventricular gradient, etc. Still further, the sensor may be equipped to detect LAP, LVP, RVP, PPG or S1 heart sounds. It should be understood that multiple separate sensors can be provided and, depending upon the parameter to be detected, at least some of the sensor might be positioned external to the device housing.

The device additionally includes a battery 810, which provides operating power to all of the circuits shown in FIG. 12. The battery 810 may vary depending on the capabilities of device 10. If the system only provides low voltage therapy, a lithium iodine or lithium copper fluoride cell typically may be utilized. For device 10, which employs shocking therapy, the battery 810 should be capable of operating at low current drains for long periods, and then be capable of providing high-current pulses (for capacitor charging) when the patient requires a shock pulse. The battery 810 should also have a predictable discharge characteristic so that elective replacement time can be detected. Accordingly, appropriate batteries are employed.

As further shown in FIG. 12, device 10 is shown as having an impedance measuring circuit 812, which is enabled by the microcontroller 760 via a control signal 814. Uses for an impedance measuring circuit include, but are not limited to, detecting cardiogenic impedance for the purposes of detecting the onset of isovolumic ventricular contraction; lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 812 is advantageously coupled to the switch 874 so that any desired electrode may be used.

In the case where device 10 is intended to operate as an ICD device, it detects the occurrence of an arrhythmia, and automatically applies an appropriate electrical shock therapy to the heart aimed at terminating the detected arrhythmia. To this end, the microcontroller 760 further controls a shocking circuit 816 by way of a control signal 818. The shocking circuit 816 generates shocking pulses of low (up to 0.5 joules), moderate (0.5-10 joules) or high energy (11 to 40 joules or more), as controlled by the microcontroller 760. Such shocking pulses are applied to the heart of the patient through at least two shocking electrodes, and as shown in this embodiment, selected from the left atrial coil electrode 728, the RV coil electrode 736, and/or the SVC coil electrode 738. The housing 740 may act as an active electrode in combination with the RV electrode 736, or as part of a split electrical vector using the SVC coil electrode 738 or the left atrial coil electrode 728 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 760 is capable of controlling the synchronous or asynchronous delivery of the shocking pulses.

Insofar as the optimization of VV delays is concerned, the microcontroller includes a standalone VV optimization controller 801 operative to perform or control all or some of the 'standalone' techniques of FIGS. 2-9, described above. Optimizer 801 includes a QRS peak detector 803, an onset of isovolumic ventricular mechanical contraction (VC) detector 805 and a T_QtoVC detector 807, which is operative to detect the time delay from the peak of the QRS to the onset of isovolumic ventricular mechanical contraction. A T_QtoVC-based VV optimization system 809 determines preferred or optimal values for VV based on the techniques discussed above. The standalone optimization technique can exploit optimized AV/PV delay values received via the telemetry circuit or determined by the device itself using an IEGM-based AV/PV/VV optimization system 819.

Additionally or alternatively, the microcontroller includes a combined VV optimization controller 811 operative to perform or control all or some of the 'combined' techniques of FIG. 9, described above. The combined optimization technique can exploit initial optimized VV delay values determined by IEGM-based AV/PV/VV optimization system 819 (or received via telemetry.) Still further, the microcontroller also includes a T_QtoVC-based vector optimization system 813 operative to perform or control all or some of the vector optimization techniques of FIG. 10, described above. The microcontroller additionally includes a T_QtoVC-based CRT nonresponder detection system 815 operative to identify CRT nonresponders using the techniques described above and/or detect or track heart failure and its progression within the patient. CRT is controlled by a CRT controller 817. An internal warning device 799 may be provided for generating perceptible warning signals to the patient via vibration, voltage or other methods. Diagnostic data may be recorded in memory 794.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

As noted, at least some of the techniques described herein can be performed by (or under the control of) an external device. For the sake of completeness, an exemplary device programmer will now be described, which includes components for controlling at least some of the functions and steps already described.

Exemplary External Programmer

Figure 13:
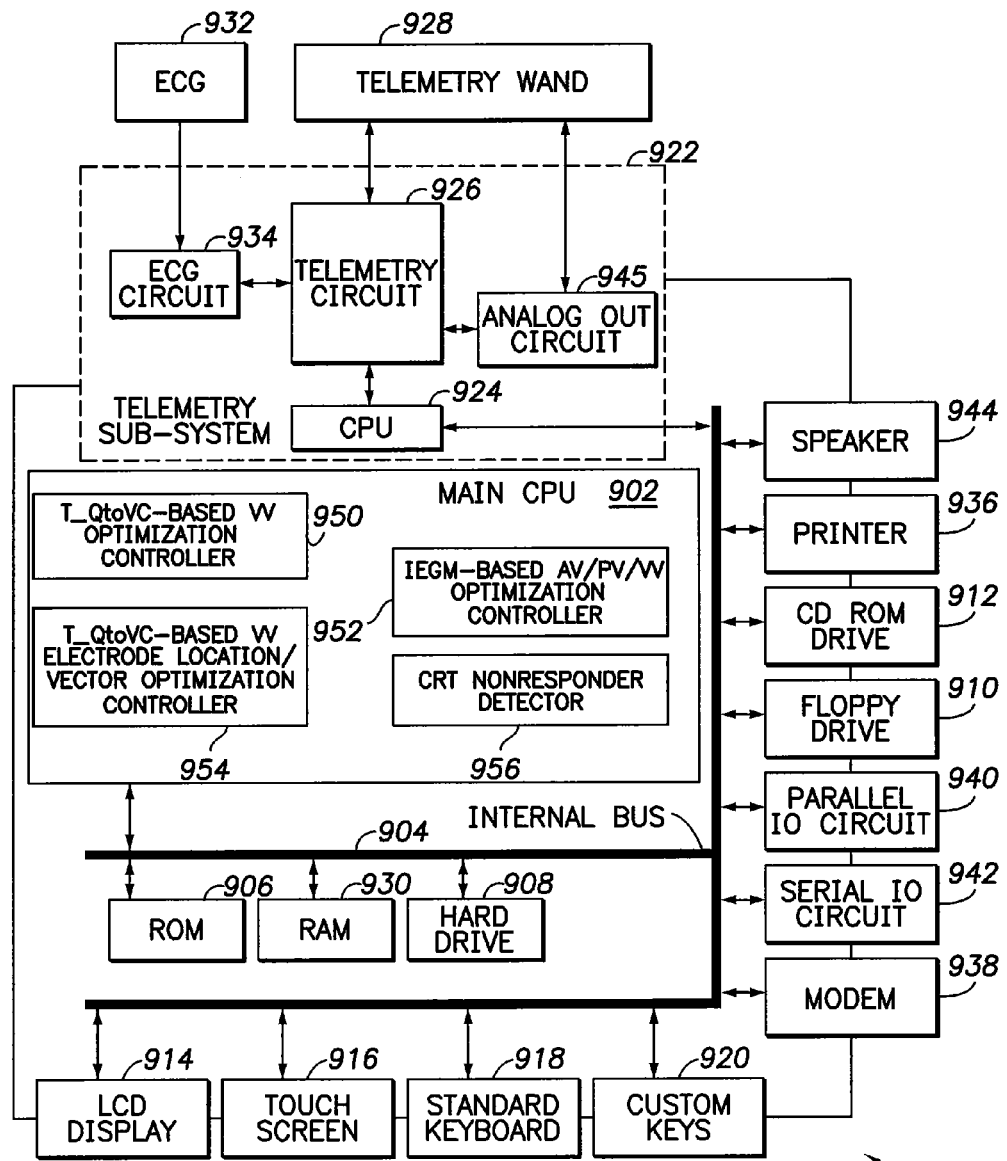
FIG. 13 is a functional block diagram illustrating components of the external device programmer of FIG. 1 and particularly illustrating programmer-based optimization components for controlling the various optimization techniques.

FIG. 13 illustrates pertinent components of an external programmer 14 for use in programming the device of FIG. 12 and for performing or controlling the above-described optimization techniques. For the sake of completeness, other device programming functions are also described herein. Generally, the programmer permits a physician, clinician or other user to program the operation of the implanted device and to retrieve and display information received from the implanted device such as IEGM data and device diagnostic data. Additionally, the external programmer can be optionally equipped to receive and display ECG data from separate external surface ECG leads that may be attached to the patient. Depending upon the specific programming of the external programmer, programmer 14 may also be capable of processing and analyzing data received from the implanted device and from the ECG leads to, for example, render preliminary diagnosis as to medical conditions of the patient or to the operations of the implanted device.

Now, considering the components of programmer 14, operations of the programmer are controlled by a CPU 902, which may be a generally programmable microprocessor or microcontroller or may be a dedicated processing device such as an ASIC or the like. Software instructions to be performed by the CPU are accessed via an internal bus 904 from a read only memory (ROM) 906 and random access memory 930. Additional software may be accessed from a hard drive 908, floppy drive 910, and CD ROM drive 912, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 914 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 916 overlaid on the LCD display or through a standard keyboard 918 supplemented by additional custom keys 920, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 14 to retrieve data stored within any implanted devices and to also retrieve ECG data from ECG leads, if any, coupled to the patient. To this end, CPU 902 transmits appropriate signals to a telemetry subsystem 922, which provides components for directly interfacing with the implanted devices, and the ECG leads. Telemetry subsystem 922 includes its own separate CPU 924 for coordinating the operations of the telemetry subsystem. Main CPU 902 of programmer communicates with telemetry subsystem CPU 924 via internal bus 904. Telemetry subsystem additionally includes a telemetry circuit 926 connected to telemetry wand 928, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an ECG circuit 934 for receiving surface ECG signals from a surface ECG system 932. In other implementations, the ECG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the device also includes the data stored within the recalibration database of the device (assuming the device is equipped to store that data.) Data retrieved from the implanted devices is stored by external programmer 14 either within a random access memory (RAM) 930, hard drive 908 or within a floppy diskette placed within floppy drive 910. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 14, the implanted devices may be further controlled to transmit additional data in real time as it is detected by the implanted devices, such as additional IEGM data, lead impedance data, and the like. Additionally, or in the alternative, telemetry subsystem 922 receives ECG signals from ECG leads 932 via an ECG processing circuit 934. As with data retrieved from the implanted device itself, signals received from the ECG leads are stored within one or more of the storage devices of the external programmer. Typically, ECG leads output analog electrical signals representative of the ECG. Accordingly, ECG circuit 934 includes analog to digital conversion circuitry for converting the signals to digital data appropriate for further processing within the programmer. Depending upon the implementation, the ECG circuit may be configured to convert the analog signals into event record data for ease of processing along with the event record data retrieved from the implanted device. Typically, signals received from the ECG leads are received and processed in real time.

Thus, the programmer receives data both from the implanted devices and from optional external ECG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 902, the programming commands are converted to specific programmable parameters for transmission to the implanted devices via telemetry wand 928 to thereby reprogram the implanted devices. Prior to reprogramming specific parameters, the physician may control the external programmer to display any or all of the data retrieved from the implanted devices or from the ECG leads, including displays of ECGs, IEGMs, and statistical patient information. Any or all of the information displayed by programmer may also be printed using a printer 936.

Additionally, CPU 902 also includes a T_QtoVC-based VV optimization system 950 operative to determine preferred or optimal values for VV pacing based on the techniques discussed above, including either the standalone optimization techniques of FIGS. 2-8 or the combined optimization techniques of FIG. 9. As explained, these techniques can exploit an initial set of AV/PV/VV delay values determined via IEGM-based optimization techniques. Accordingly, an IEGM-based optimization controller 952 may be employed to determine initial values for AV/PV and/or VV delays, which are then used to further refine the VV delays using the optimization techniques already described. Also, CPU 902 includes a T_QtoVC-based electrode location/vector optimization controller operative to perform or control all or some of the electrode location/vector optimization techniques of FIG. 10, described above. The CPU additionally includes a T_QtoVC-based CRT nonresponder detector 956 operative to perform or control all or some of the CRT nonresponder identification techniques, described above in connection with FIG. 11.

Depending upon the implementation, the various components of the CPU may be implemented as separate software modules or the modules may be combined to permit a single module to perform multiple functions. In addition, although shown as being components of the CPU, some or all of these components may be implemented separately using ASICs or the like.

Programmer/monitor 14 also includes a modem 938 to permit direct transmission of data to other programmers via the public switched telephone network (PSTN) or other interconnection line, such as a T1 line or fiber optic cable. Depending upon the implementation, the modem may be connected directly to internal bus 904 may be connected to the internal bus via either a parallel port 940 or a serial port 942. Other peripheral devices may be connected to the external programmer via parallel port 940 or a serial port 942 as well. Although one of each is shown, a plurality of input output (I/O) ports might be provided. A speaker 944 is included for providing audible tones to the user, such as a warning beep in the event improper input is provided by the physician. Telemetry subsystem 922 additionally includes an analog output circuit 945 for controlling the transmission of analog output signals, such as IEGM signals output to an ECG machine or chart recorder.

With the programmer configured as shown, a physician or other user operating the external programmer is capable of retrieving, processing and displaying a wide range of information received from the implanted device and to reprogram the implanted device if needed. The descriptions provided herein with respect to FIG. 13 are intended merely to provide an overview of the operation of programmer and are not intended to describe in detail every feature of the hardware and software of the programmer and is not intended to provide an exhaustive list of the functions performed by the programmer.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable cardiac rhythm management device for implant within a patient, the method comprising:
   detecting ventricular electrical depolarization within the patient based on electrocardiac signals sensed by the device;
   detecting an onset of isovolumic ventricular mechanical contraction within the patient based on cardiomechanical signals sensed by the device;
   determining a time delay from ventricular electrical depolarization to the onset of isovolumic ventricular mechanical contraction;
   setting interventricular (VV) pacing delays so as to minimize the time delay; and
   controlling pacing based on the VV pacing delays.

2. The method of claim 1 wherein detecting ventricular electrical depolarization events is performed to detect a peak of a depolarization waveform (QRS complex) so that the determined time delay is representative of a delay (T_QtoVC) between the peak of the QRS and the onset of isovolumic ventricular contraction (VC).

3. The method of claim 2 wherein detecting ventricular electrical depolarization events is performed using an intracardiac electrogram (IEGM) signal sensed within the left ventricle (LV).

4. The method of claim 2 wherein detecting the onset of isovolumic ventricular contraction includes:
   detecting values representative of electrical cardiogenic impedance (Z) within the patient;
   detecting the onset of isovolumic ventricular mechanical contraction within the Z values.

5. The method of claim 2 wherein setting VV pacing delays based on T_QtoVC includes:
   setting a preferred VV delay to a value sufficient to yield a minimal T_QtoVC time delay.

6. The method of claim 5 wherein setting the preferred VV delay to a value sufficient to yield a minimal T_QtoVC time delay includes:
   selectively varying the VV delay while measuring the T_QtoVC time delay to determine the VV delay yielding the shortest T_QtoVC time delay.

7. The method of claim 1 wherein the device is equipped to employ hybrid vectors that include a large field vector and wherein the onset of isovolumic ventricular contraction is detected using the hybrid vectors.

8. The method of claim 7 wherein the large field vector includes one or more of an SVC-can vector, an RV ring to can vector and an RV ring to SVC coil vector.

9. The method of claim 1 wherein detecting ventricular mechanical contractions includes:
   detecting values representative of one or more of left atrial pressure (LAP), right ventricular pressure (RVP), left ventricular pressure (LVP), photo-plethysmography (PPG) signals and heart sounds within the patient; and
   detecting the onset of ventricular mechanical contraction from the detected values.

10. The method of claim 1 further including tracking heart failure progression based on changes over time in the time delay from ventricular electrical depolarization to the onset of isovolumic ventricular mechanical contraction.

11. The method of claim 1 wherein all of the steps are performed by the implantable medical device.

12. The method of claim 1 wherein at least some of the steps are performed by an external device based on signals received from the implantable medical device.

13. A system for use with an implantable cardiac rhythm management device for implant within a patient, the system comprising:
   a ventricular electrical depolarization detection system operative to detect ventricular electrical depolarization within the patient;
   a ventricular mechanical contraction detection system operative to detect an onset of isovolumic ventricular mechanical contraction within the patient;
   an electromechanical time delay determination system operative to determine a time delay between ventricular electrical depolarization and the onset of ventricular mechanical contraction;
   an interventricular (VV) pacing delay determination system operative to set VV pacing delays based on the time delay between ventricular electrical depolarization and the onset of ventricular mechanical contraction; and
   a pacing controller operative to control pacing based on the VV pacing delays.

* * * * *